United States Patent
Mallick et al.

(10) Patent No.: US 6,622,569 B2
(45) Date of Patent: Sep. 23, 2003

(54) INSTRUMENTED MOLD FOR USE IN MATERIAL TESTING EQUIPMENT FOR MEASUREMENT OF MATERIAL PROPERTIES

(75) Inventors: Rajib B. Mallick, Holden, MA (US); Matthew R. Teto, Fitchburg, MA (US)

(73) Assignee: Pine Instrument Company, Grove City, PA (US)

( * ) Notice: Subject to any disclaimer, the term of this patent is extended or adjusted under 35 U.S.C. 154(b) by 0 days.

(21) Appl. No.: 09/803,867

(22) Filed: Mar. 12, 2001

(65) Prior Publication Data

US 2001/0054318 A1 Dec. 27, 2001

Related U.S. Application Data

(60) Provisional application No. 60/188,376, filed on Mar. 10, 2000.

(51) Int. Cl.[7] .................................................. G01N 3/08
(52) U.S. Cl. ........................................................ 73/824
(58) Field of Search ............................. 264/40.5, 40.1, 264/328.1, 40.7; 73/818, 819, 821, 823, 824, 825

(56) References Cited

U.S. PATENT DOCUMENTS

| | | | | |
|---|---|---|---|---|
| 4,047,425 A | | 9/1977 | Handy et al. | |
| 4,434,655 A | * | 3/1984 | Summerfield et al. | ........ 73/167 |
| 4,604,906 A | * | 8/1986 | Scarpa | ..................... 73/861.74 |
| 4,848,926 A | * | 7/1989 | Jenkins | ........................ 374/142 |
| 5,303,602 A | * | 4/1994 | Morgan | ..................... 73/866.5 |
| 5,663,508 A | * | 9/1997 | Sparks | ..................... 73/861.71 |
| 5,733,486 A | * | 3/1998 | Hayasi et al. | .............. 264/40.1 |
| 5,792,960 A | * | 8/1998 | Lewis et al. | .................. 73/786 |
| 6,060,005 A | * | 5/2000 | Hettinga | .................... 264/40.5 |

* cited by examiner

Primary Examiner—Max Noori
(74) Attorney, Agent, or Firm—Roetzel & Andress

(57) ABSTRACT

A system and method for measuring forces and behavior of a material when subjected to an applied force in a contained vessel or mold in directions not aligned with the applied force. Materials which flow, including mixed materials with an aggregate and a mastic, can be tested within a material vessel or mold by applying a force to the material within the mold and, in addition to measuring resistance of the material to the applied force, resulting forces applied by the material to the mold walls, for example laterally relative to the applied force, are measured and are indicative of flow characteristics and load bearing performance, and shear strength of the material. In a specific testing device, a material testing mold for use with material testing equipment which applies forces to material within the mold, has a mold cavity formed by walls. At least one portion of the wall is configured to deflect or deform in response to material pressure created by a force applied to the material. Deflection or deformation of the mold wall is measured to provide an indication of force transfer load bearing properties and behavior of the material in the mold, which is indicative of real world performance.

34 Claims, 16 Drawing Sheets

Gyration versus ratio of horizontal to vertical pressure (pL/pV) and voids in total mix (VTM) for mixes with different nominal maximum aggregate size Voids filled with asphalt (VFA) versus ratio of horizontal to vertical pressure (pL/pV) for 9.5 mm coarse mix Voids in total mix (%) versus ratio of horizontal to vertical pressure (pL/pV) for two samples of stone matrix asphalt (SMA)

Voids filled with asphalt (VFA) versus ratio of horizontal to vertical pressure (pL/pV) for two samples of stone matrix asphalt (SMA)

Voids filled with asphalt (VFA) versus ratio of horizontal to vertical pressure (pL/pV) for SMA and HMA (9.5 mm coarse mix)

Gyration versus ratio of horizontal to vertical pressure (pL/pV) and voids in total mix (VTM) plot for 9.5 mm mix with rounded aggregates Voids in total mix (VTM) versus ratio of horizontal to vertical pressure (pL/pV) for 9.5 mm coarse mix with rounded aggregates Gyration versus ratio of horizontal to vertical pressure (pL/pV) 9.5 mm coarse mixes with angular and rounded aggregates Voids in total mix (VTM) versus ratio of horizontal to vertical pressure (pL/pV) for 9.5 mm coarse mixes with angular and rounded aggregate Voids filled with asphalt (VFA) versus ratio of horizontal to vertical pressure (pL/pV) for mixes with angular and rounded aggregates

US 6,622,569 B2

INSTRUMENTED MOLD FOR USE IN MATERIAL TESTING EQUIPMENT FOR MEASUREMENT OF MATERIAL PROPERTIES

RELATED APPLICATIONS

This application claims priority to U.S. Ser. No. 60/188,376, filed Mar. 10, 2000.

FIELD OF THE INVENTION

The present invention pertains generally to materials testing and, more particularly, to machinery and methods for applying forces to materials and measuring material responses to applied forces.

BACKGROUND OF THE INVENTION

Materials testing frequently involves subjecting a material specimen, held in a container or mold, to a variety of forces and analyzing the material response to such forces. In certain types of materials testing equipment, material is held in a rigid cavity or vessel and subjected to substantial force. One inherent limitation of such testing is that by confining a material specimen within a rigid structure such as a mold, it is difficult to detect or measure forces exerted by the material in multiple dimensions or directions. The mold allows measurement of a material response in only a single dimension, which yields data on only certain properties of the material. Measurement of material response in multiple dimensions can yield valuable information on material properties, and in some cases data which corresponds more accurately to the real world characteristics and performance of a material.

In one particular type of materials testing, a composite material may be made up of a mix of a binding/filler material (or "mastic") and an aggregate. Under pressure, the aggregate will shift according to the amount of voids or air pockets in the binding material and according to shear forces between the binding material and aggregate surfaces. Such composite materials are commonly tested by compression within a mold or cavity. Standard testing procedures measure the resistance of the mix to compression only in a single dimension, e.g. resistance to the compressive force. This type of measurement does not account for the lateral forces acting against the cavity walls. A means for measuring the response of a material to an applied force in multiple directions would yield additional useful data on material properties.

One example of a composite material having an aggregate and a fluid binding agent is asphalt mix used for road surfaces, also referred to as hot mix asphalt or "HMA". Known methods for testing the load bearing properties of asphalt involve compaction of an asphalt sample within a mold by a ram driven axially into the mold. Other methods involve movement or gyration of the mold as material is compacted within, as described for example in U.S. Pat. No. 5,456,118, incorporated herein by reference. Asphalt material properties, such as behavior under traffic loads, are deduced from the force applied to the compaction ram, the response or extent of compaction of the mix and from the forces required to gyrate the mold. Because the walls of the mold are rigid, such testing methods do not account for reaction of the material laterally against the mold walls, or in directions other than along the axis of compression. There exists a need to overcome this deficiency of prior art testing methods and equipment.

Identification of tenderness potential (tendency of a material mix to push and shove during in-place compaction) permits rectification through better mix design or modified construction procedure saving a considerable amount of time, energy and money during field rolling of hot mix asphalt (HMA) and cold asphalt mixes. Accurate determination of rutting potential (permanent deformation) of mixes can prevent construction of rut susceptible pavements and associated maintenance and replacement costs. Numerous studies have shown that the rutting potential of HMA increases significantly with an increase in asphalt content and an increase in the percentage of rounded aggregates. Studies have also shown that rutting potential of HMA increases significantly as the air voids drop below two percent. Experience from all over the world also indicates that stone matrix asphalt (SMA) has significantly less rutting potential compared to dense graded HMA, even at low air voids. To date many theories and equipment have been developed to simulate the phenomenon of rutting in the laboratory and hence to predict the rutting potential of mixes. However, no theory or equipment has so far been completely successful in predicting rutting potential of asphalt mixes in a way which matches the performance of in-place mixes.

At present there is a need for a single tool that can predict the tenderness and rutting potential of asphalt paving mixes accurately. Furthermore, there is a need for a tool that can accurately identify the rutting potential of mixes at different air voids (voids in mix, VTM).

SUMMARY OF THE PRESENT INVENTION

It is therefore an object of the present invention to provide a tool that can be used to: determine rutting potential of mixes; to determine tenderness potential of mixes; to determine ideal design air voids for different mixes; to compare different asphalt binders; to compare different aggregates; to compare different gradations; and to control quality of mixes during production and laydown.

The invention provides in one aspect a newly developed tool, a lateral pressure indicator (LPI), for predicting tenderness and rutting potential of composite or mixed materials, such as asphalt paving mixes. The present invention provides a material testing method and system in which the response of a material to an applied force is measured in a direction other than that of a force applied to the material. In accordance with one general aspect of the invention, there is provided a system and method for measurement of reaction of a material in multiple dimensions in response to an applied force, and methods for determining material properties from the measured reactions. In one example of the invention, lateral pressure of a mix material generated as a result of a vertical or non-aligned applied pressure or force is measured. Materials which exert a high lateral pressure relative to an applied vertical pressure are identified as having an accompanying low shear strength. In the case of an asphalt/aggregate mix proposed for use as a paving surface, the measured lateral pressure and shear strength properties are predictive of the performance of the asphalt mix in a real traffic environment.

In one embodiment of a material testing system of the invention, a device is provided for measuring reactive forces of a material subjected to a testing force. The device comprises a mold capable of housing material to be tested adapted for use with material testing equipment. The mold has a mold wall, a portion of which has an aperture defined by a perimeter within the mold wall area. The aperture in the mold wall is configured to accept an insert piece. A sensor is provided for measuring the force exerted on an insert piece by material in the mold.

In one specific embodiment of a material testing mold of the invention, for use in connection with material testing equipment operative to apply a force to material within the mold and to gyrate the mold as the force is applied, the mold has a mold cavity defined by a mold wall and an opening through which a compaction ram enters the mold to compact material within the mold, a portion of the mold wall being movable in a direction generally orthogonal to a direction of compaction of material within the mold by the material testing equipment. One or more sensors such as load cells are operatively connected to the movable portion of the mold wall to sense a force exerted on the movable portion of the mold wall by the material compacted in the mold.

In another specific embodiment of a material testing mold of the invention, for use in connection with material testing equipment, the mold has a mold cavity defined by a continuous mold wall. A portion of the mold wall is configured to deflect or otherwise dynamically respond to a force exerted on the wall by material within the mold which is under a compaction force applied by the material testing equipment to the material within the mold. The portion of the mold wall configured to deflect or dynamically respond to pressure of material under compaction within the mold is instrumented to measure a force exerted by the material upon the wall. The measured force is indicative of physical properties and load bearing characteristics of the material in the mold, including shear strength.

DETAILED DESCRIPTION OF PREFERRED AND ALTERNATE EMBODIMENTS

A simple way of measuring the shear strength in a composite material is through the measurement of lateral pressure that is generated due to a vertical pressure. For example, a solid block of steel, loaded below its crushing strength, would develop almost negligible lateral pressure under a vertical stress, whereas in a mass of water, with no shear strength, the lateral pressure that is developed due to a vertical pressure is equal to the vertical pressure. The example of these two extreme cases illustrate that for a material which lies, in material properties, somewhere between a solid block of steel and mass of water, the higher the lateral pressure due to a vertical pressure, the lower the shear strength of the material.

In soil mechanics, it is well known that a soil with rounded aggregates would result in a low angle of internal friction ($\phi$), and hence a low shear strength. From the concepts of lateral pressure developed in soil (as applied to retaining walls, for example), it can be shown that the ratio of lateral to vertical pressure at rest ($K_o$) can be represented by:

$$K_o = 1 - \sin \phi$$

which indicates that the higher the value of $\phi$, the lower the value of $K_o$, and visa versa. Hence a high lateral pressure in soil would indicate a low $\phi$, and hence a low shear strength.

From the above discussion it seems that a change in generation of lateral pressure during loading of asphalt mixes should indicate a change in shear strength, and a difference in lateral pressure between two different mixes should indicate a difference in shear strength that is generated in the two mixes. Similarly, a difference in lateral pressure between asphalt mixes with the same asphalt content would be a means to indicate any difference in $\phi$ due to a difference in aggregate particle shape or difference in gradation of aggregates.

Figure 1:
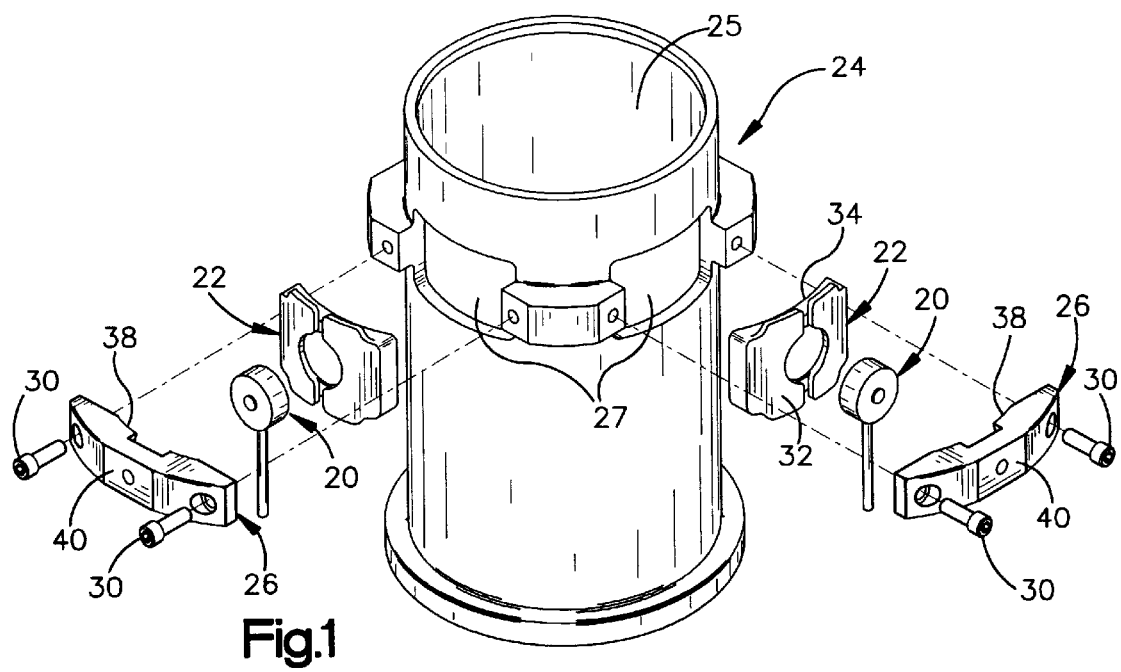
FIG. 1 shows one embodiment of a lateral pressure indicator of the present invention.
Figure 2A:
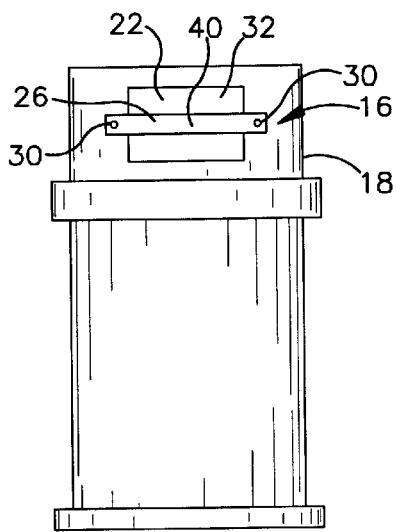
FIG. 2 shows a lateral pressure indicator load cell for one embodiment the present invention.
Figure 2C:
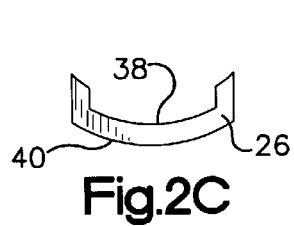
Figure 2D:
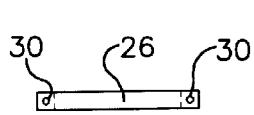
Figure 2E:
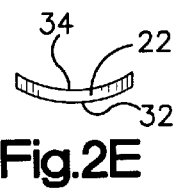
Figure 2F:
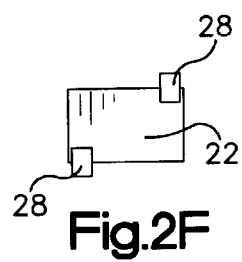
Figure 2B:
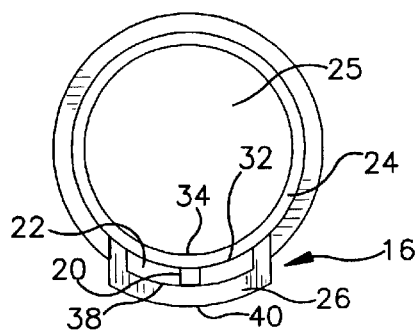

According to the present invention, a lateral pressure indicator (LPI) is provided for determination of force resulting from the application of a testing force on a material. FIG. 1 shows one embodiment of an LPI configured for use with a Superpave gyratory compactor (SGC), although it should be understood that the LPI can be configured for use with any type of compactor. The LPI comprises a mold 24 configured for use with a compactor. The mold 24 is generally cylindrical, having a cavity 25 configured to hold testing material. In the present embodiment, the mold 24 is steel, although it can be constructed from any material able to withstand abrasion resulting from the application of testing force to asphalt, as well as continuous heating and cooling without deforming.

The mold 24 has a mold wall 29 with at least one aperture 27 configured to accept an insert piece 22. The aperture 27 is defined by a perimeter within the mold wall 29. Preferably, the mold has two apertures 27 spaced apart radially. In the present embodiment, the mold has two apertures spaced apart by approximately ninety degrees. However, there can be more apertures in the mold, and the present invention is not limited to ninety degree separation. For each aperture 27, an insert piece 22 is configured to match the aperture 27. The insert piece 22 has an exterior surface 32 and an interior surface 34. In the present embodiment, the insert piece 22 is generally rectangular, however, it may be of any shape (i.e. circular, ovular, triangular. The insert piece 22 is curved so that the interior surface 34 matches the contours of the mold wall 29 when the insert piece 22 is placed in aperture 27. The exterior surface 32 is configured to interact with a sensor 20. In the present embodiment, each aperture has a single sensor 20, a load cell, however, the sensor 20 may be a strain gauge or any other sensor capable of measuring applied force. In addition, each aperture may have multiple sensors 20 for measuring force. The insert piece 22 can be made from any material strong enough to resist deformation when subjected to force resulting from the application of a testing force on a material inside a cavity in the mold. In the current embodiment, the insert piece 22 is steel.

Attached to mold 24 on the sides of aperture 27 is a bracket 26. The bracket 26 is secured to mold 24 on the external side of mold 24 by hex-head screws 30, however, other types of screws, pins, bolts, or the like may also be used. In the present embodiment, the bracket 26 is secured to mold 24 so as to form a gap between an exterior surface 32 of insert piece 22 and an interior surface 38 of bracket 26. The interior surface 38 is designed to interact with load cell 20, which resides between the exterior surface 32 of insert piece 22 and the interior surface 38 of bracket 26.

When the material testing equipment is in operation, testing force is applied to a testing material, which creates a resulting force that pushes outward on the interior surfaces of mold 24 and insert pieces 22. The sensor 20 measures this resulting force. The resulting force measurements from sensor 20 are then relayed to a digital readout, although an analog readout may also be used. Knowing the surface areas of the components upon which force is applied, lateral pressure and shear strength of the testing material can be extrapolated from the force measurements.

Referring now to FIG. 2, an alternate embodiment of the present invention is depicted. The LPI shown in FIG. 2 functions as does the one shown in FIG. 1. However, the invention of FIG. 2 has only one aperture 27.

Figure 3:
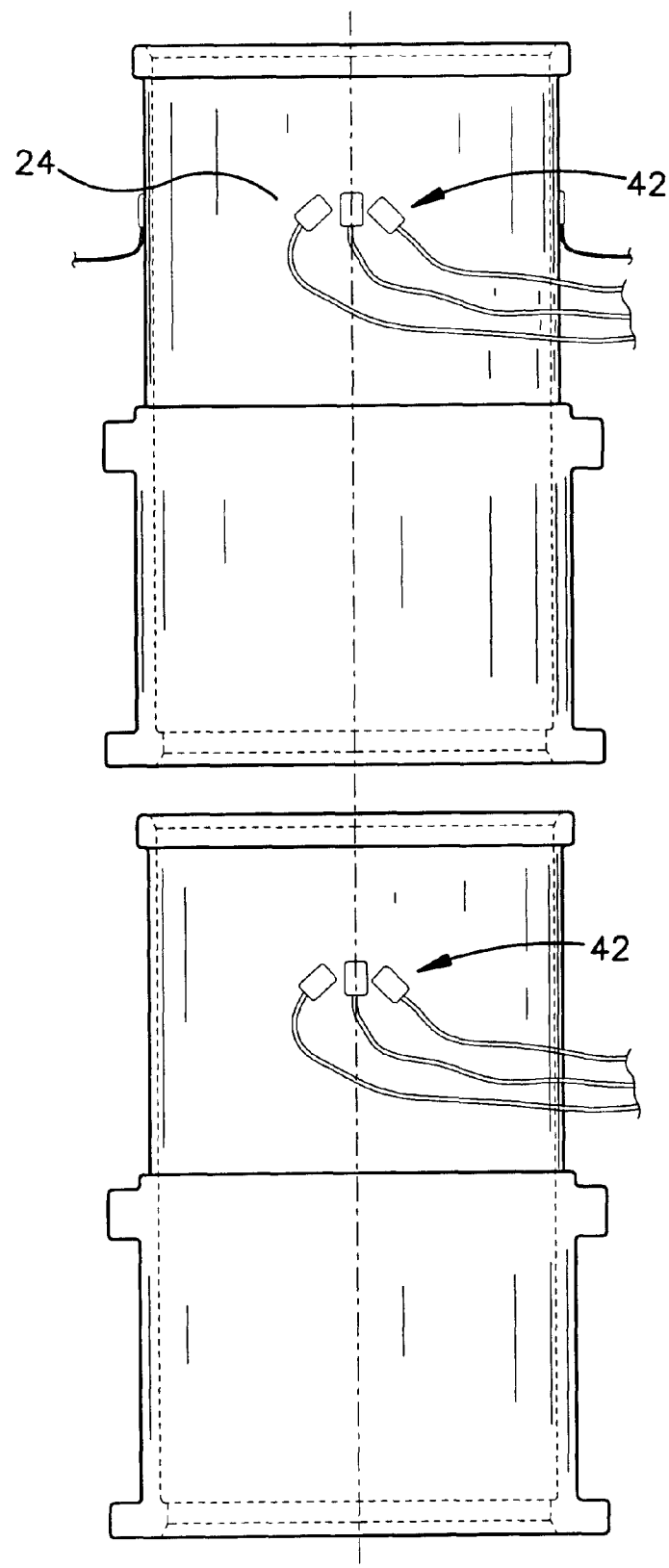
FIG. 3 shows an alternate embodiment of a lateral pressure indicator.

Referring now to FIG. 3, another embodiment of an LPI is shown. In this embodiment, a portion of the mold wall 24 is constructed so that it is thin enough to deform in response to force on the wall 24 resulting from testing force applied to the material. An array of sensors 42 such as strain gauges are applied to a pressure sensitive portion of the mold wall 24 to measure deformation. The invention is not limited to any particular configuration or placement of the movable or deformable portion of the mold wall 24, or the particular type of instrumentation 42 used to record deformation of the mold wall 24 in response to pressure from the material. For example, a rosette of gauges could be used in multiple locations about the mold diameter, and arranged radially and/or axially about or on the deformable wall portion. As in the other embodiments, the measured lateral force can then be used to extrapolate the shear strength of the testing material.

When using the LPI of any of FIGS. 1–3, resultant material load can be measured at predetermined gyration intervals. The material pressure at given intervals can then be calculated by dividing force over surface area. A ratio of resultant to testing pressure can then be used for analysis.

Ratios of resulting lateral pressure to vertical pressure were obtained for various types of material mixes. Mixes with 9.5 mm nominal maximum aggregate size (NMAS) fine gradation (hence referred to as 9.5 mm (fine), mixes with 9.5 mm, 12.5 mm NMAS coarse gradation, and mixes with stone matrix asphalt (SMA) gradation were compacted with the Superpave gyratory compactor (SGC), and the lateral pressures during compaction were determined.

Figure 4:
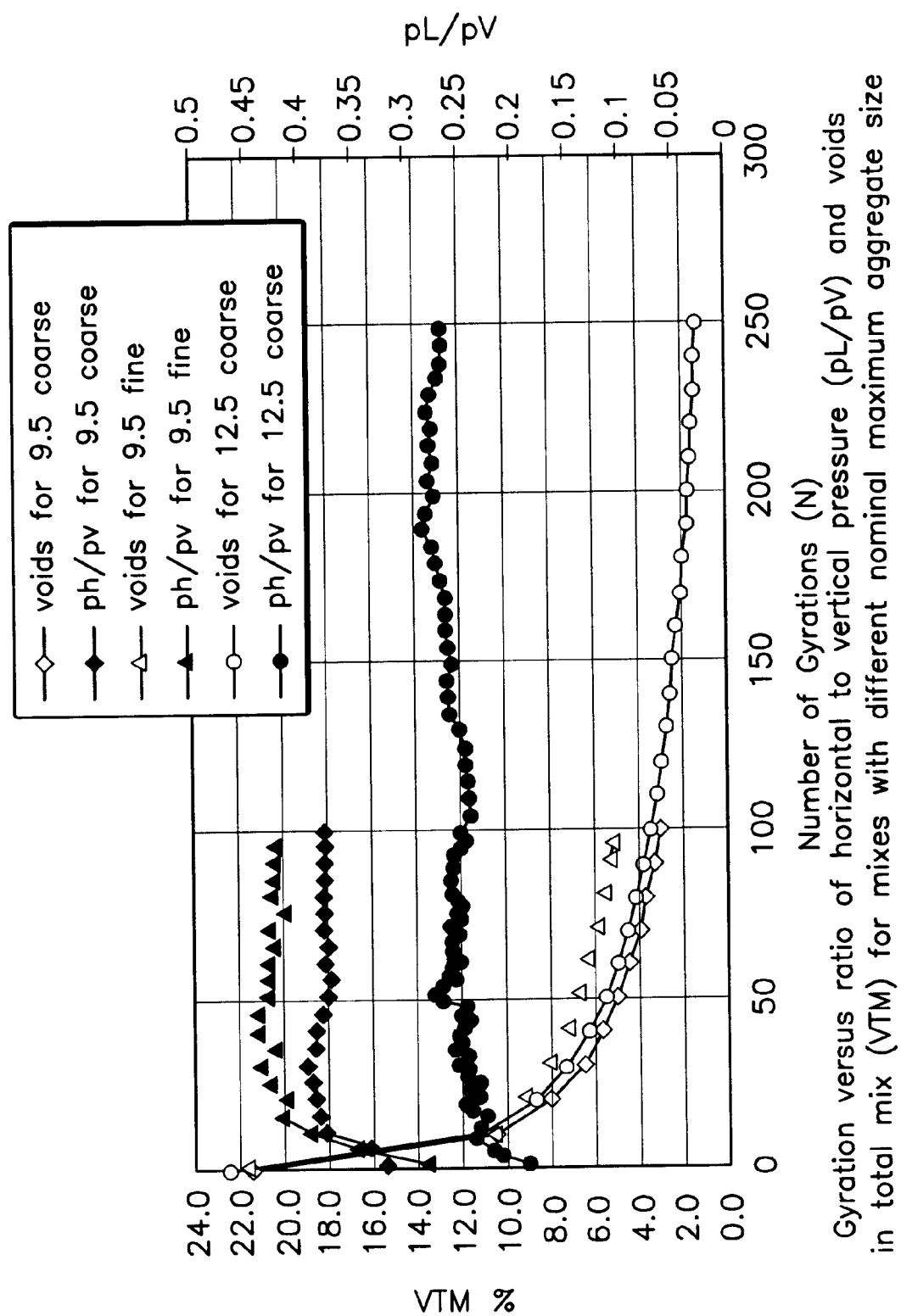
FIG. 4 is a plot of gyration versus pL/pV and VTM for mixes with different nominal maximum aggregate size.

To observe the results from mixes with different nominal maximum size aggregates, mixes with 9.5 mm coarse (asphalt content of 6.3 percent), 9.5 mm fine (asphalt content of 5.8 percent) and 12.5 mm coarse (asphalt content of 5.5 percent) gradations were compacted with the SGC, and the lateral pressure was noted during compaction. FIG. 4 shows the results. The results show that the values are different for the different mixes, and that the change in values is also different for the different mixes. It can also be seen that the 9.5 mm coarse mix has consistently less lateral pressure than the 9.5 mm fine mix, indicating a lesser amount of lateral pressure with a higher percentage of coarser materials. It should be noted that this mix shows a significantly high pL/pV value of about 0.45 between ten and seven percent voids in total mix (VTM). Since this is the range of voids from the point the mix comes under the paver and is compacted with a roller, such a high pL/pV value would indicate a potential for pushing and shoving of the mix, or tenderness, during compaction. In reality, the mix indeed showed significant tenderness problem in the field during compaction. The 12.5 mm mix shows a consistently lower pL/pV value compared to the 9.5 coarse mix. Thus FIG. 4 shows that the pL/pV values are sensitive to the nominal maximum aggregate size of the mix.

Figure 5:
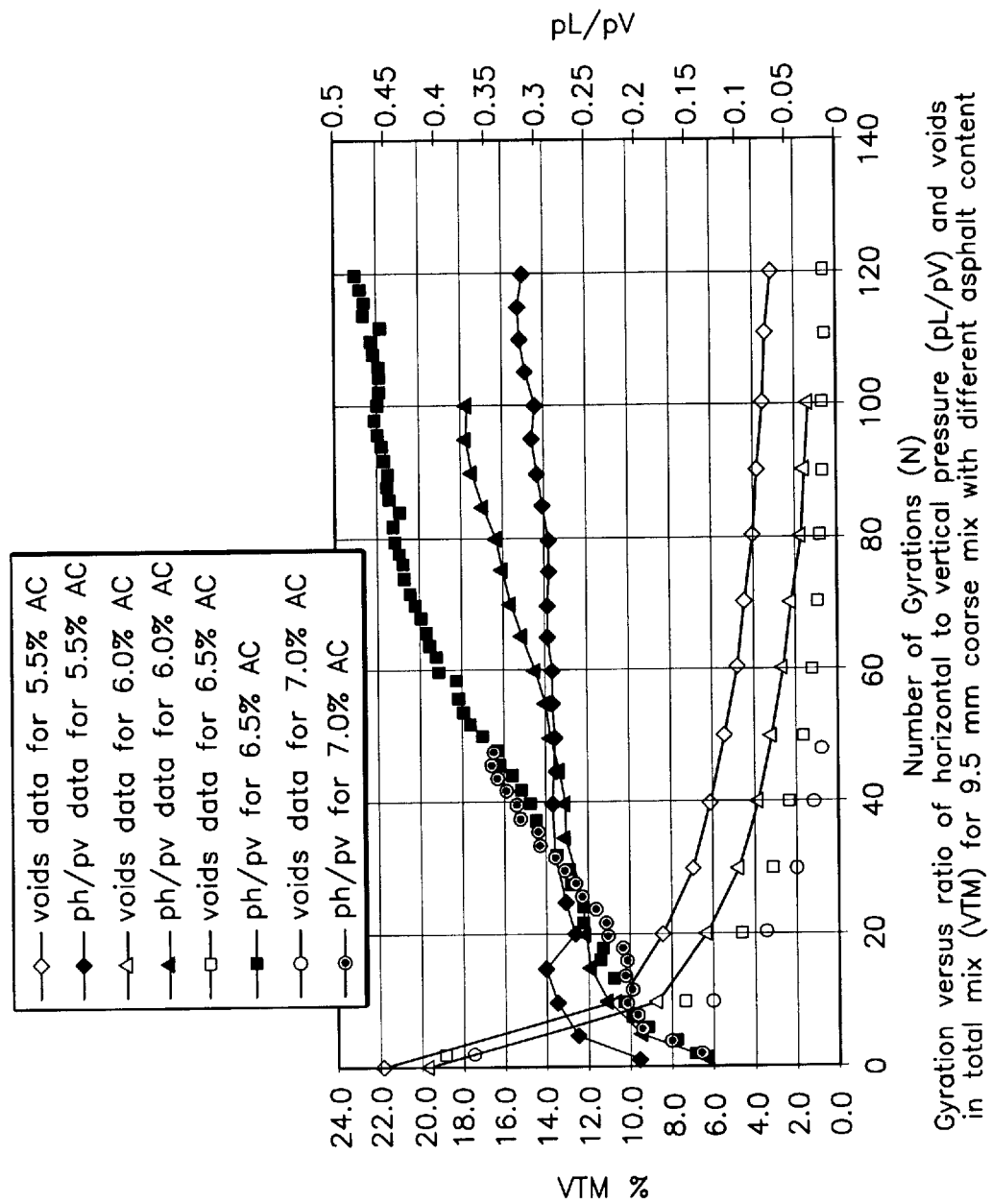
FIG. 5 is a plot of gyration versus pL/pV and VTM for 9.5 mm coarse mix with different asphalt content.
Figure 6:
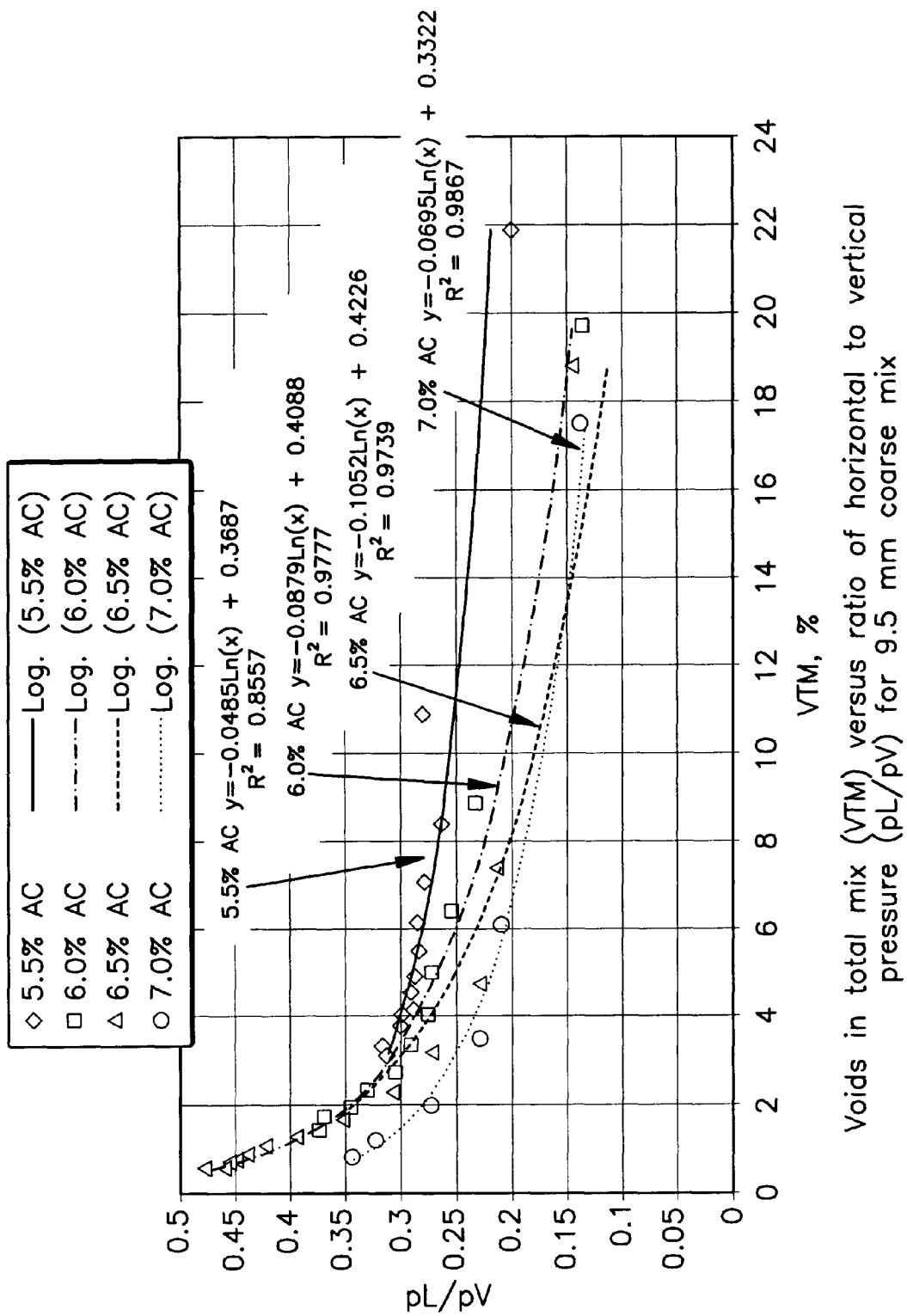
FIG. 6 is a plot of VTM versus pL/pV for 9.5 mm coarse mix.
Figure 7:
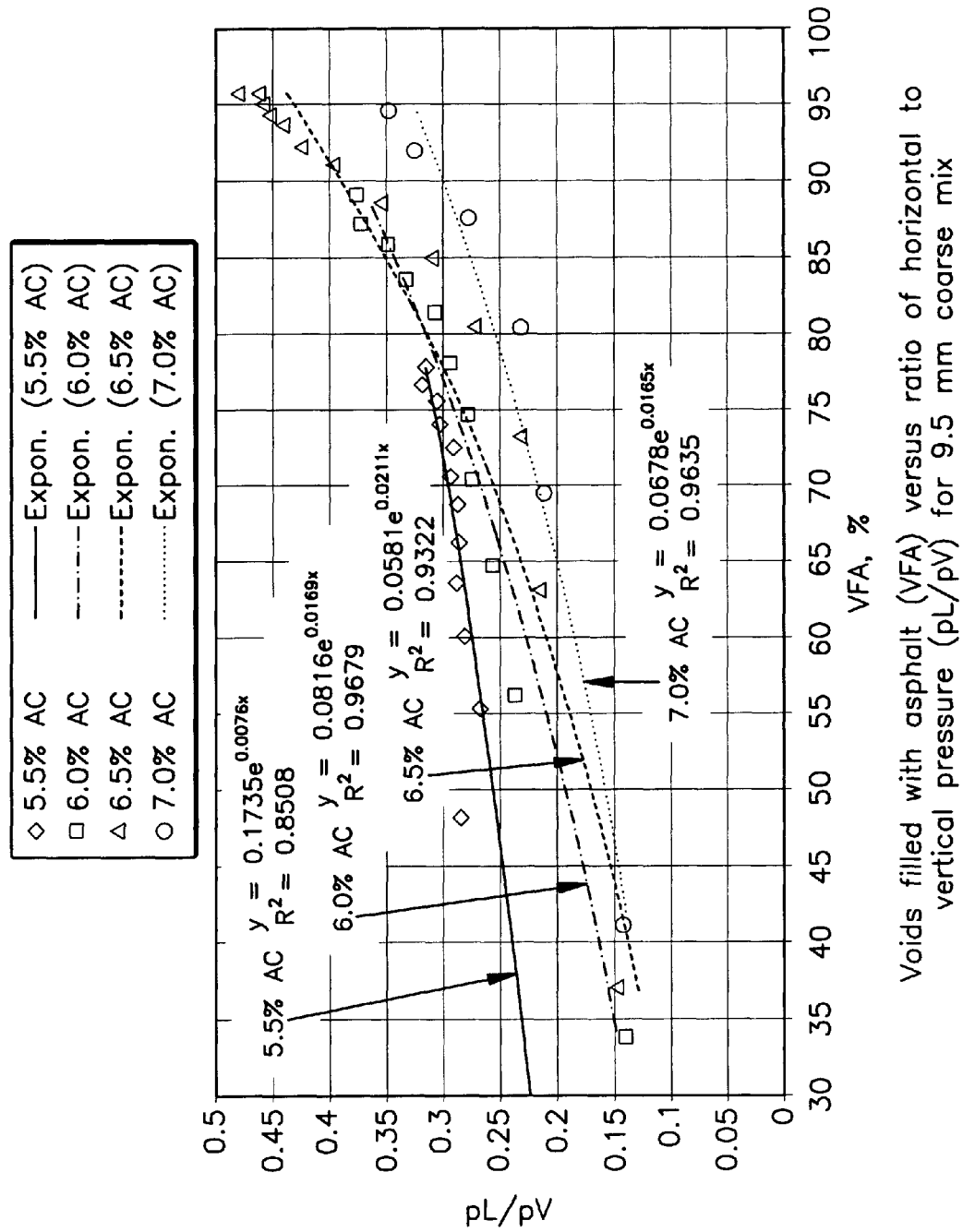
FIG. 7 is a plot of voids filled with asphalt (VFA) versus pL/pV for 9.5 mm coarse mix.

Next, samples of 9.5 mm coarse mix were compacted with different asphalt content, 5.5, 6.0, 6.5 and 7.0%, and lateral pressure was measured by the LPI FIG. 5 shows the results. It can be seen that different asphalt content mixes have different pL/pV values at any specific air voids, and the values increase significantly when the voids drop below a threshold value. A better picture is seen in FIG. 6, which shows pL/pV increasing significantly around 2 percent air voids. This matches the rutting versus air voids data that is reported in literature. FIG. 7 shows that pL/pV increases significantly at voids filled with asphalt (VFA) values around 80 percent, and that the pL/pV values increase rapidly as VFA values approach 100. Hence, the LPI yields results which are consistent with observed phenomenon of in-place rutting, as well as the proposed theory of saturation, VFA and rutting potential.

Figure 8:
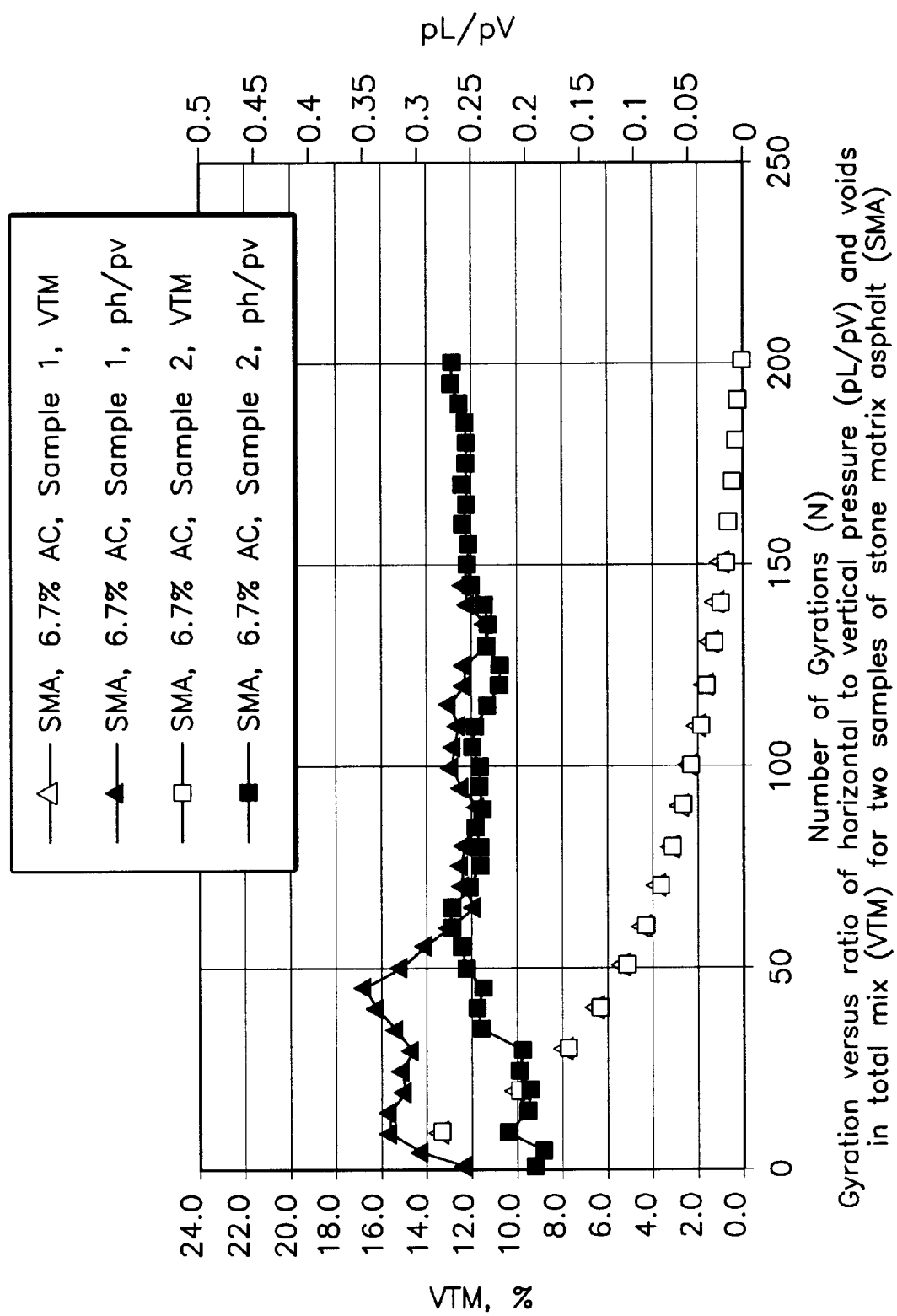
FIG. 8 is a plot of gyration versus pL/pV and VTM for two samples of stone matrix asphalt (SMA).
Figure 9:
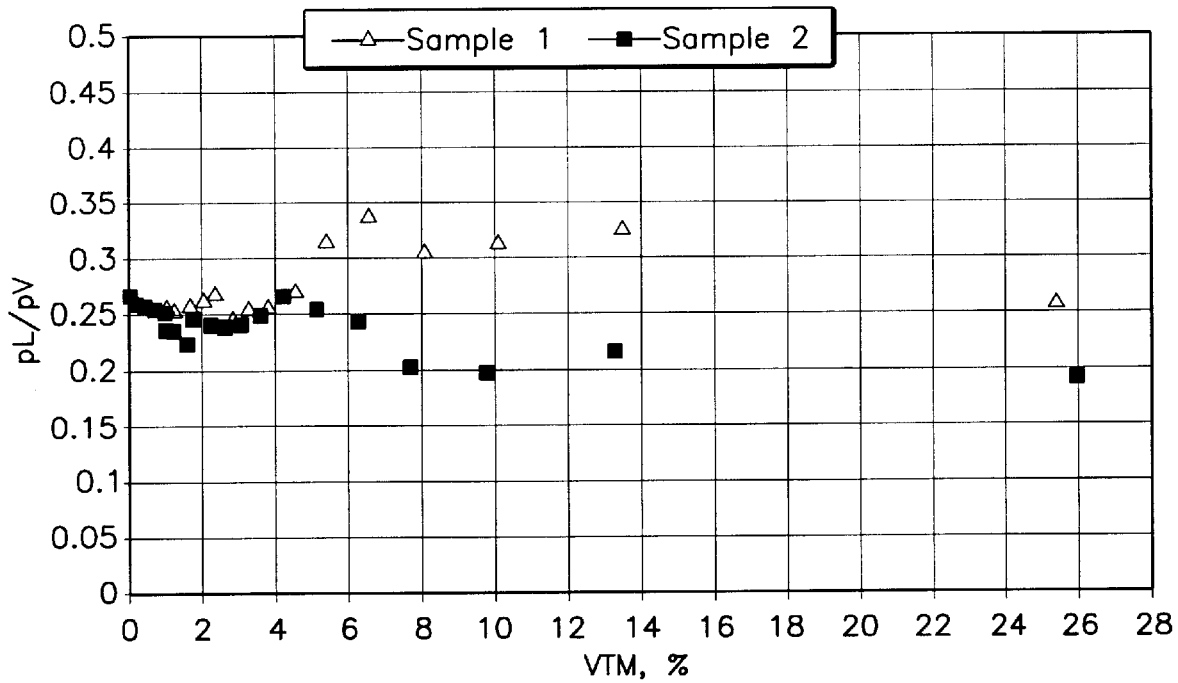
FIG. 9 is a plot of VTM versus pL/pV for two samples of SMA.
Figure 10:
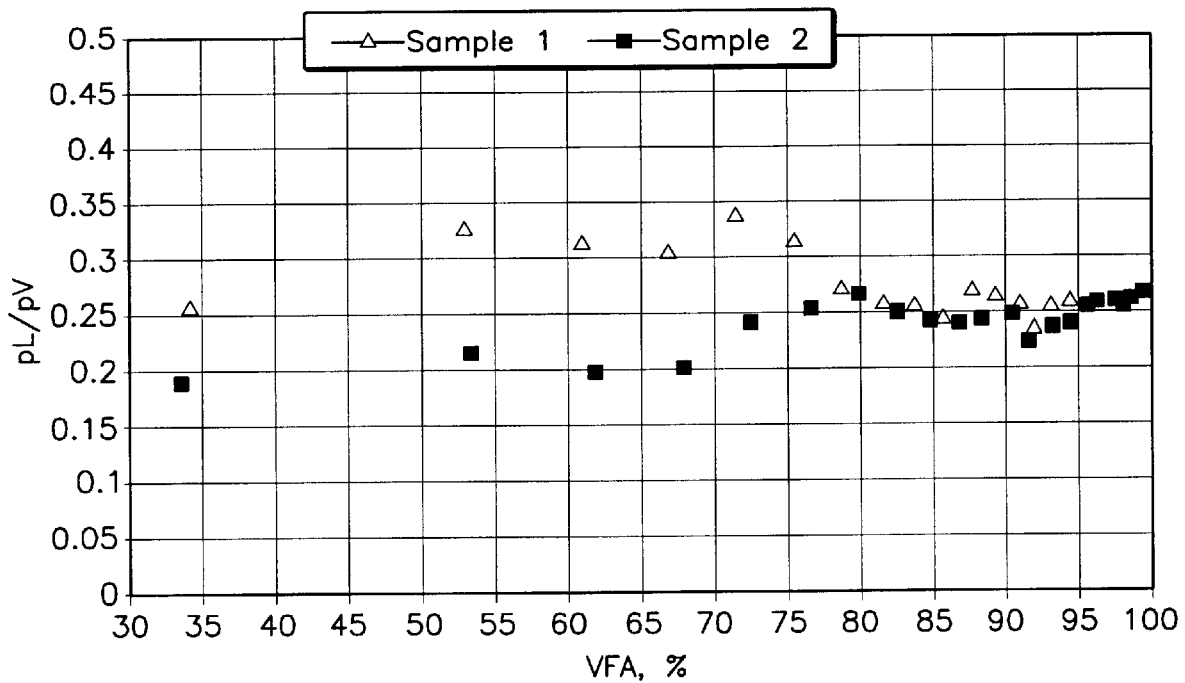
FIG. 10 is a plot of VFA versus pL/pV for two samples of SMA.
Figure 11:
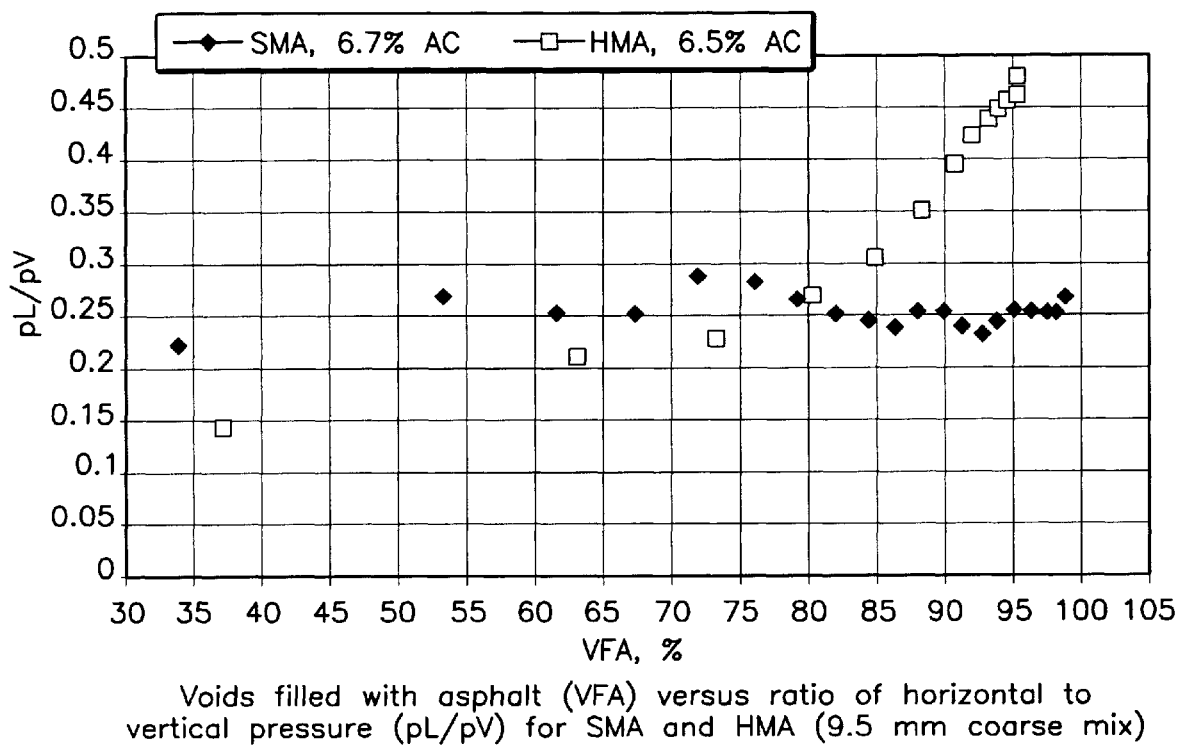
FIG. 11 is a plot of VFA versus pL/pV for 9.5 mm coarse mix SMA and 9.5 mm coarse mix HMA.

Next, two samples of a stone matrix asphalt (SMA) mix were compacted with the SGC, and the lateral pressure was measured with the LPI. Even though the values showed some difference initially, the differences become negligible above 60 gyrations, as shown in FIG. 8. FIG. 9 shows a plot of air voids versus pL/pV. The values tend to merge at around 5 percent air voids. The pL/pV values seem to be insensitive to a reduction of air voids. FIG. 10 shows that the values tend to merge at around 80 percent VFA. It can be seen that at high VFA, the pL/pV values remain below 0.3, and do not increase rapidly as VFA values approach 100. This seems to confirm the concept of stone on stone contact in SMA, and the fact that due to stone on stone contact, the major portion of the load is taken by the stone skeleton, and a negligible amount of the load is transmitted laterally and there is no build up of lateral forces. FIG. 11 shows a comparison of results from SMA and the 9.5 mm coarse aggregate mix at 6.5 percent asphalt content. It can be seen that in the case of HMA the pL/pV values take off around 80 percent VFA, where as the pL/pV value of the SMA mix remains fairly constant, and significantly below the pL/pV value of the HMA. This shows that the internal structure of the SMA mix makes the load distributed in its stone structure, whereas in the HMA a low shear strength is indicated by an increase in lateral pressure.

Figure 12:
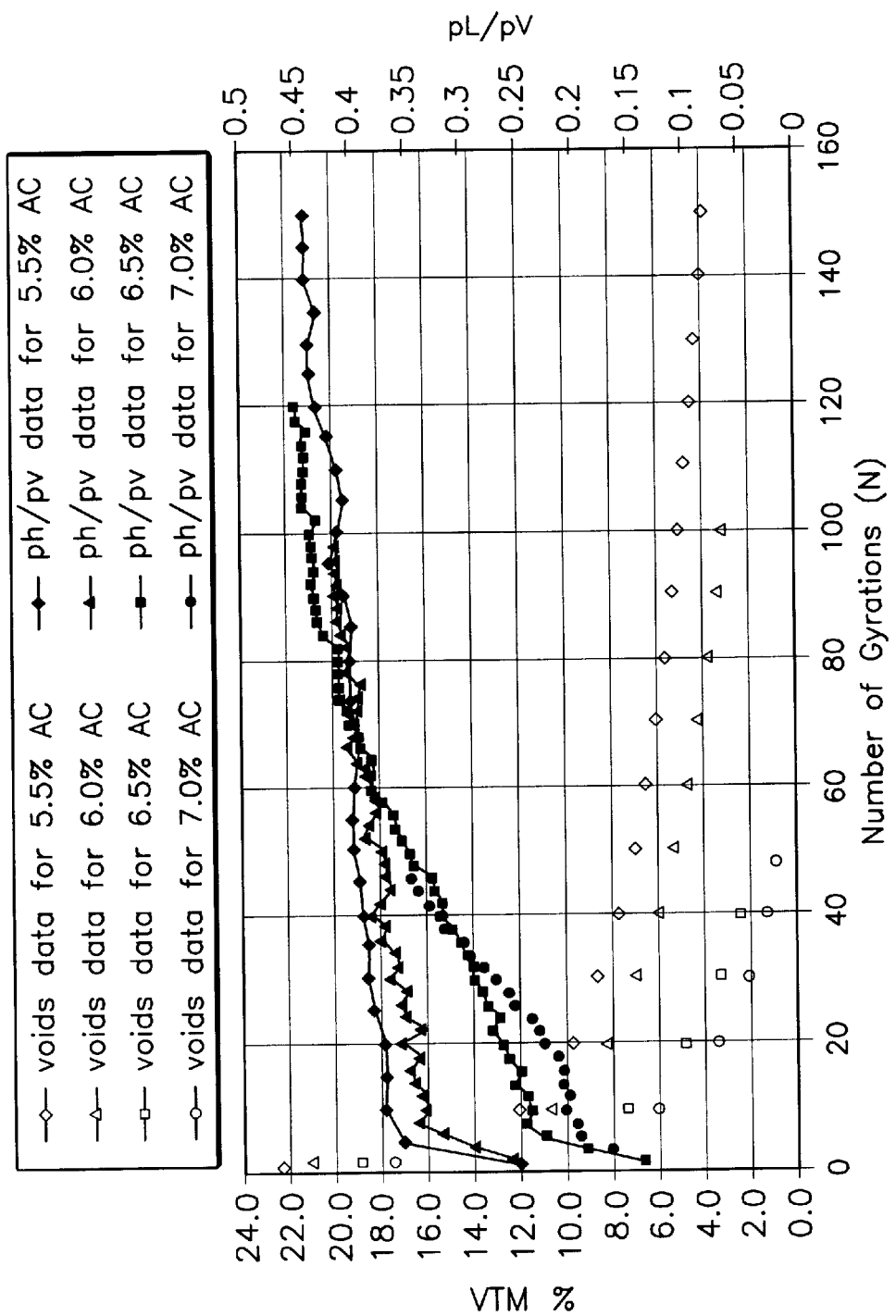
FIG. 12 is a plot of gyration versus pL/pV and (VTM) for 9.5 mm coarse mix with rounded aggregates.
Figure 13:
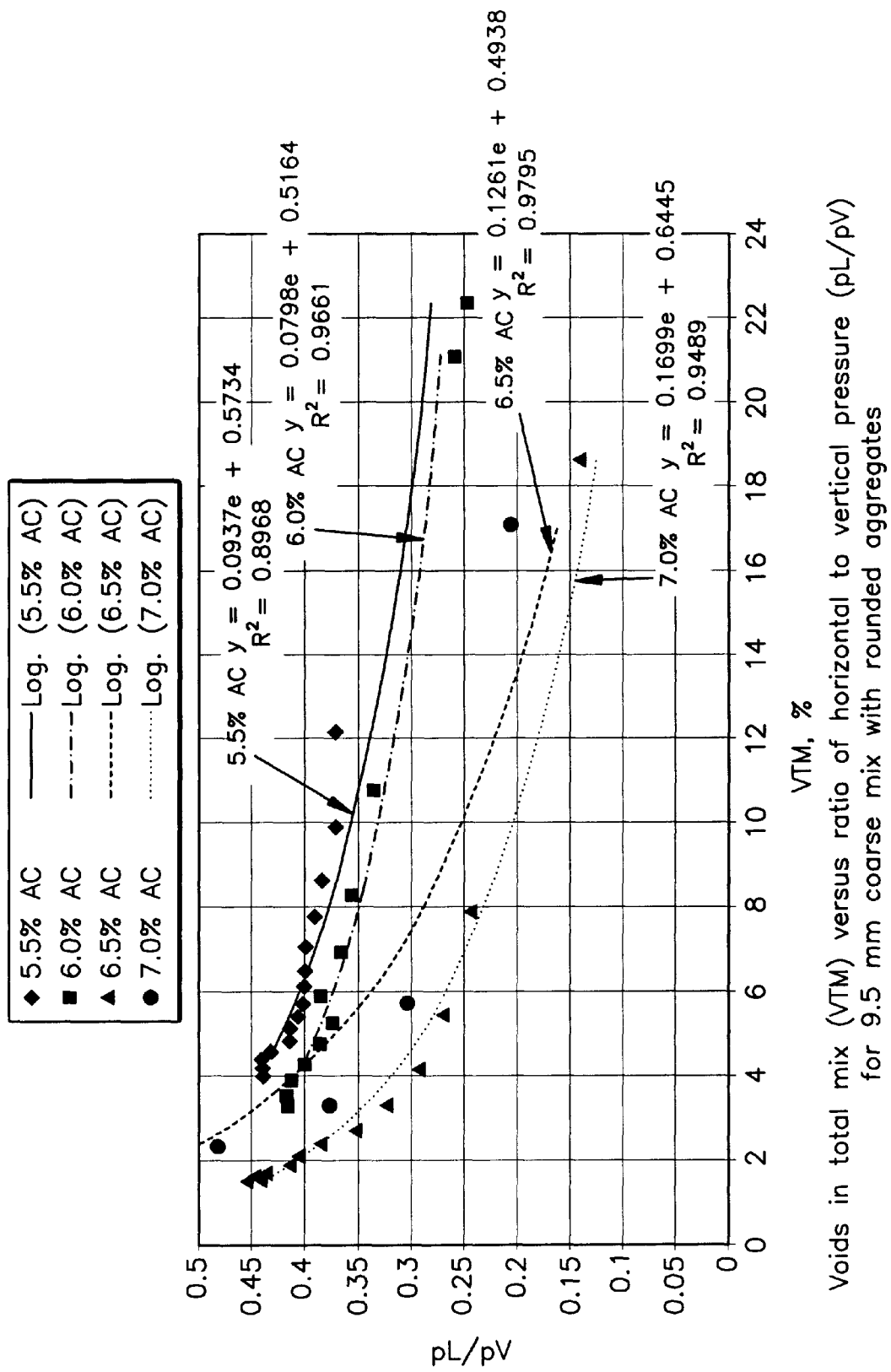
FIG. 13 is a plot of VTM versus pL/pV for 9.5 mm coarse mix with rounded aggregates.
Figure 14:
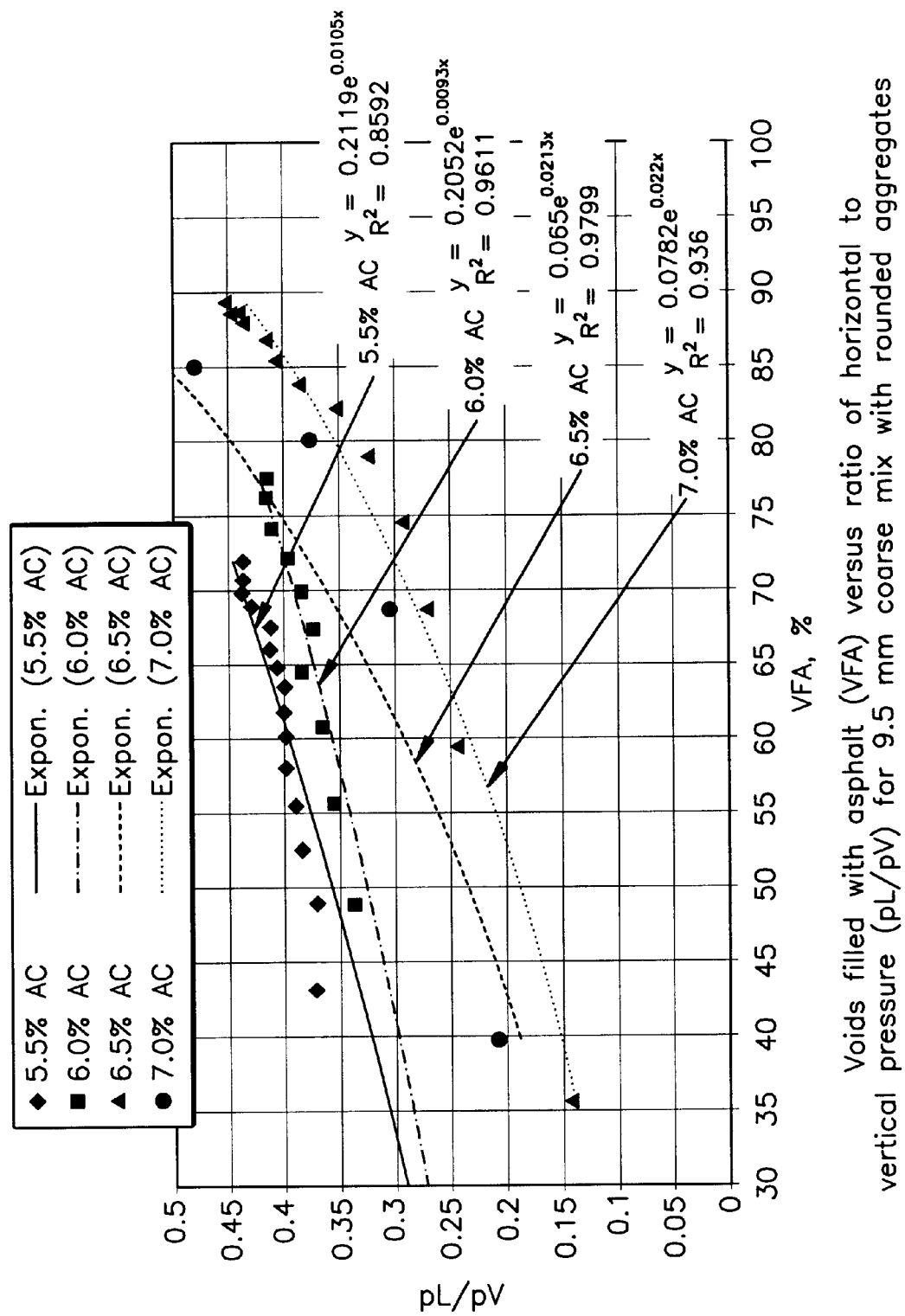
FIG. 14 is a plot of VFA versus pL/pV for 9.5 mm coarse mix with rounded aggregates.

Next, samples of 9.5 mm coarse mix with 25 percent natural sand (rounded aggregate with uncompacted voids of 35 percent) were compacted with the SGC, and the lateral pressure was determined with the LPI. FIG. 12 shows the pL/pV and air voids data versus number of gyrations. It can be seen that the pL/pV values increase with an increase in number of gyration and decrease in air voids, and at any gyration the pL/pV values are higher for the mixes with higher asphalt content. FIG. 13 shows that pL/pV increases with decrease in air voids, but mixes with different asphalt contents have different rate of increase in pL/pV—mixes with higher asphalt content show a higher rate of increase in pL/pV with a decrease in air voids. Again, this can be better explained with the help of FIG. 14, which shows that mixes with higher asphalt content actually have higher VFA, at similar air voids, and hence the data again shows the increase in pL/pV or rutting potential with an increase in saturation.

Figure 15:
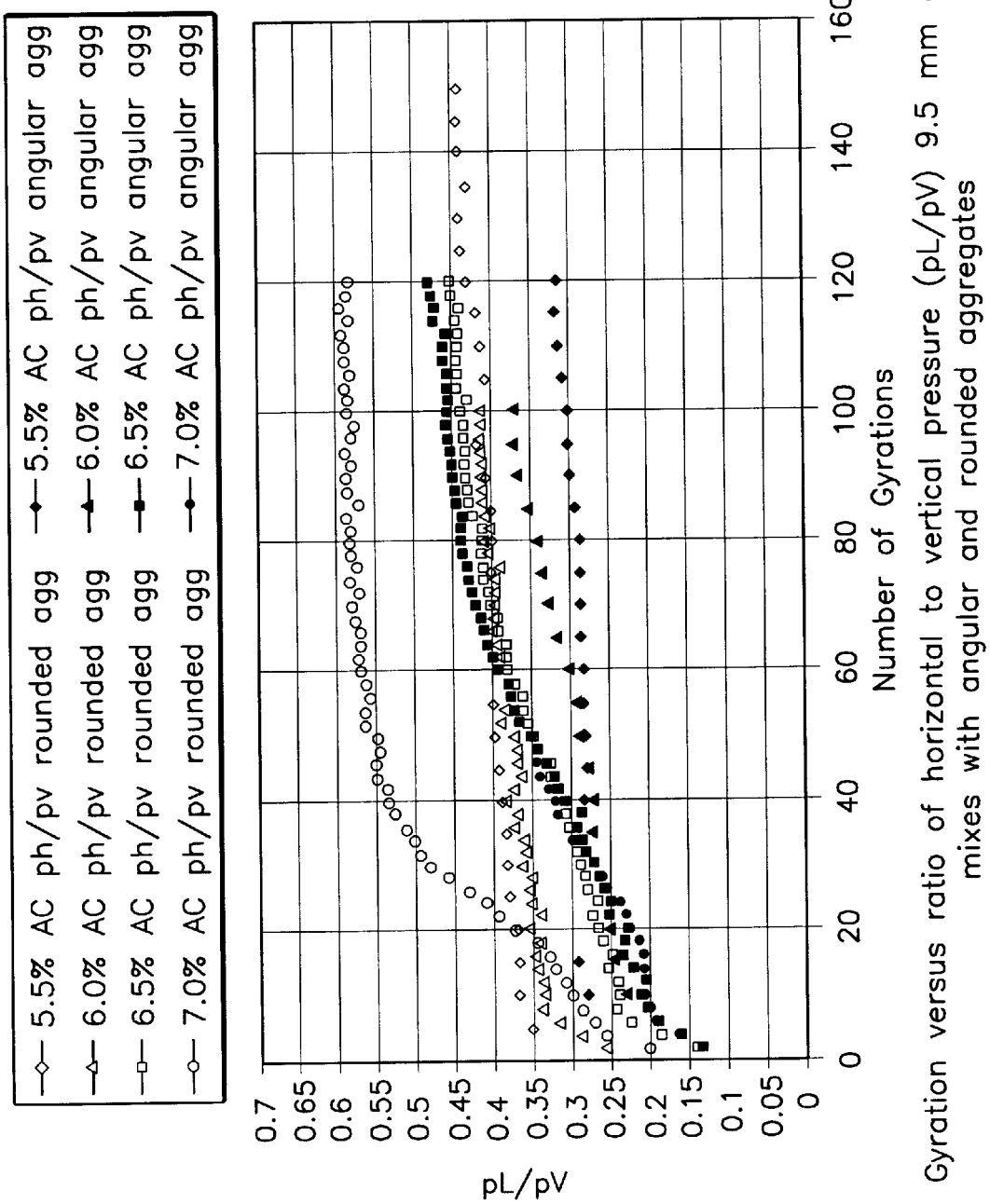
FIG. 15 is a plot of gyration versus pL/pV and (VTM) for 9.5 mm coarse mix with angular and rounded aggregates.
Figure 16:
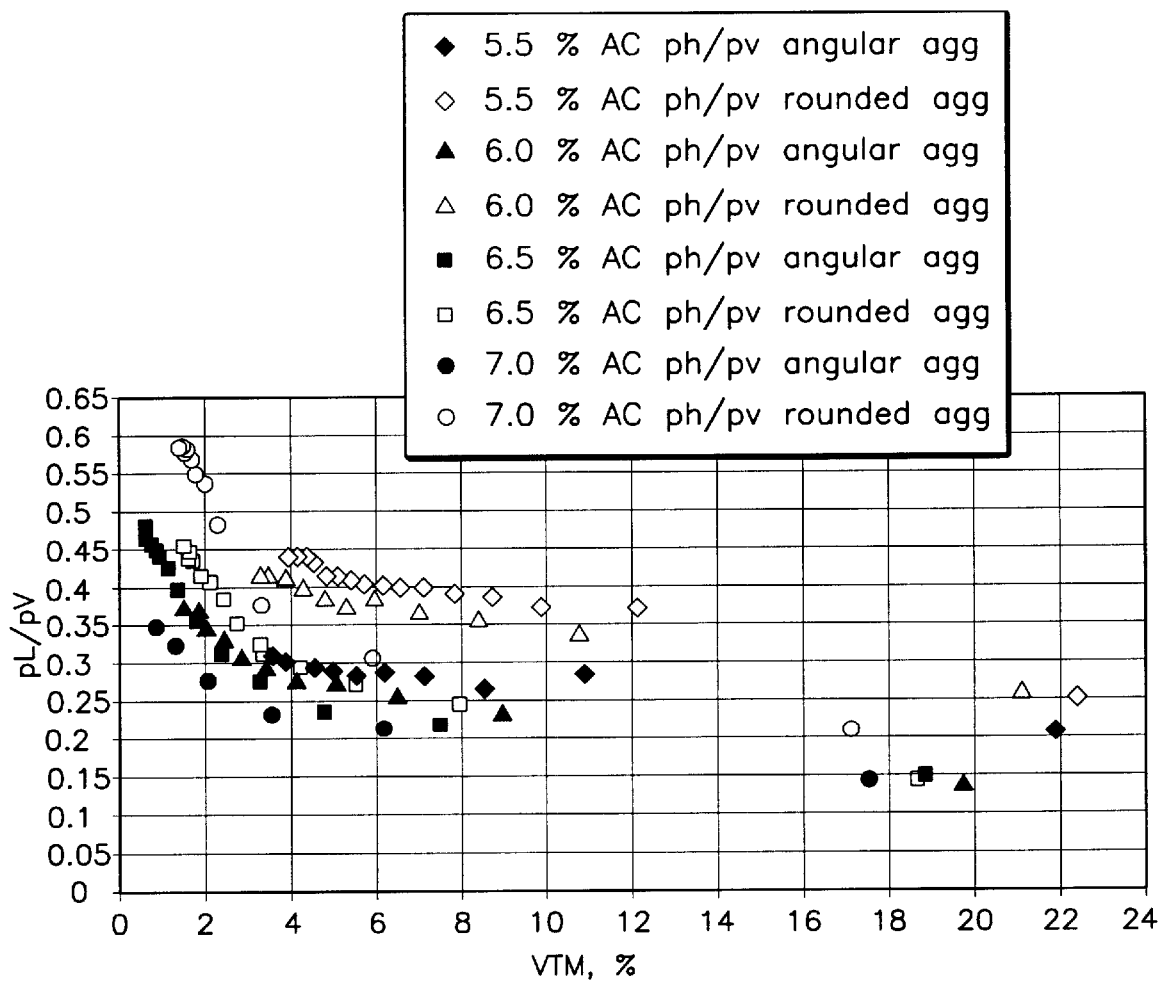
FIG. 16 is a plot of VTM versus pL/pV for 9.5 mm coarse mix with angular and rounded aggregates.
Figure 17:
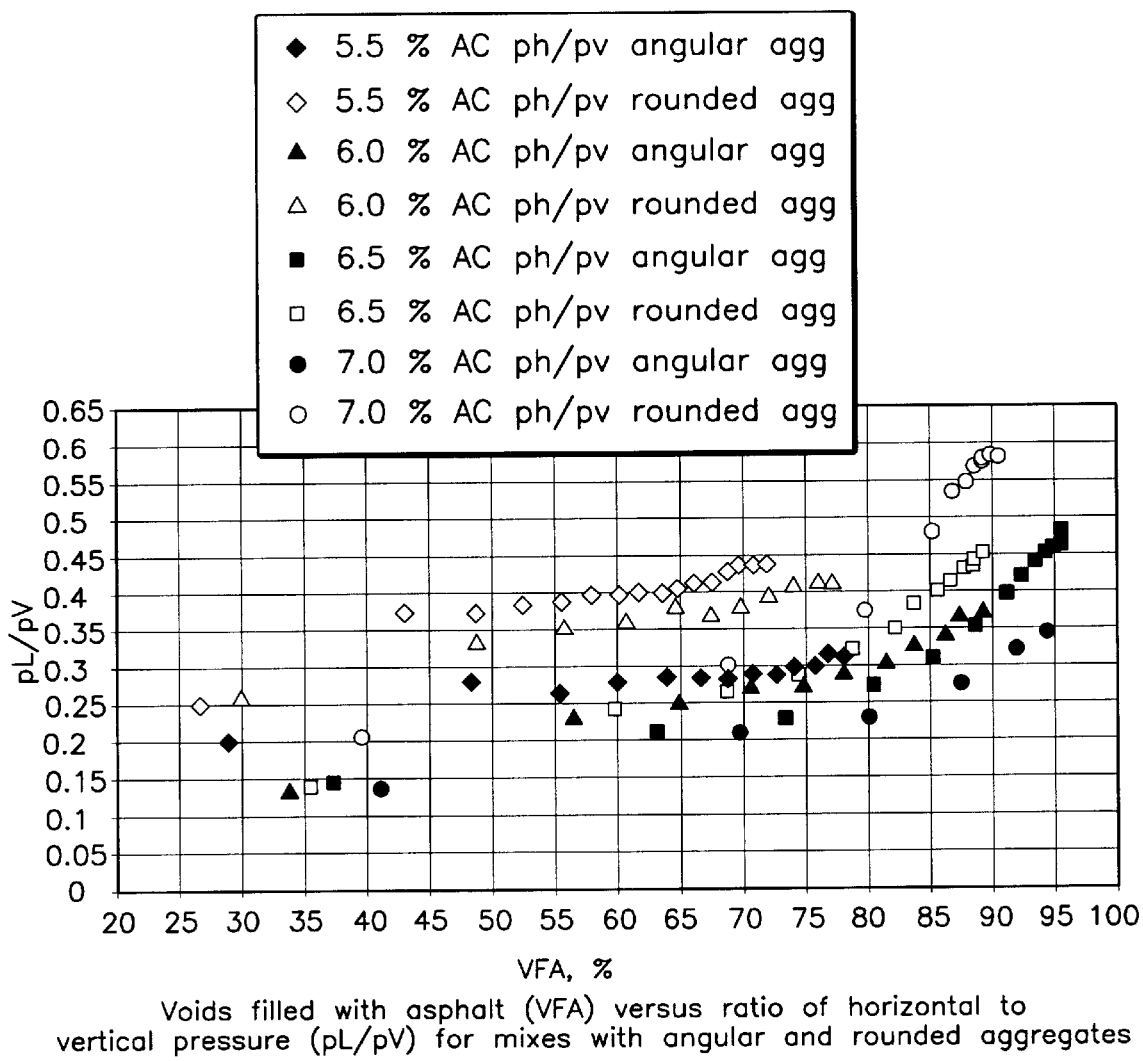
FIG. 17 is a plot of VFA versus pL/pV for 9.5 mm coarse mix with angular and rounded aggregates.

FIG. 15 shows the plots for pL/pV versus number of gyrations for 9.5 mm coarse mix with angular and rounded aggregates. It can be seen that the mix with rounded aggregates show consistently higher pL/pV values. As shown in FIGS. 16 and 17, for the same air voids and VFA, the mix with crushed angular aggregate has lower pL/pV compared to the mix with rounded aggregate. Since mixes with rounded aggregates have low values of φ, the results seem to confirm the concept of higher lateral pressure for a mix with a lower φ value.

Figure 18:
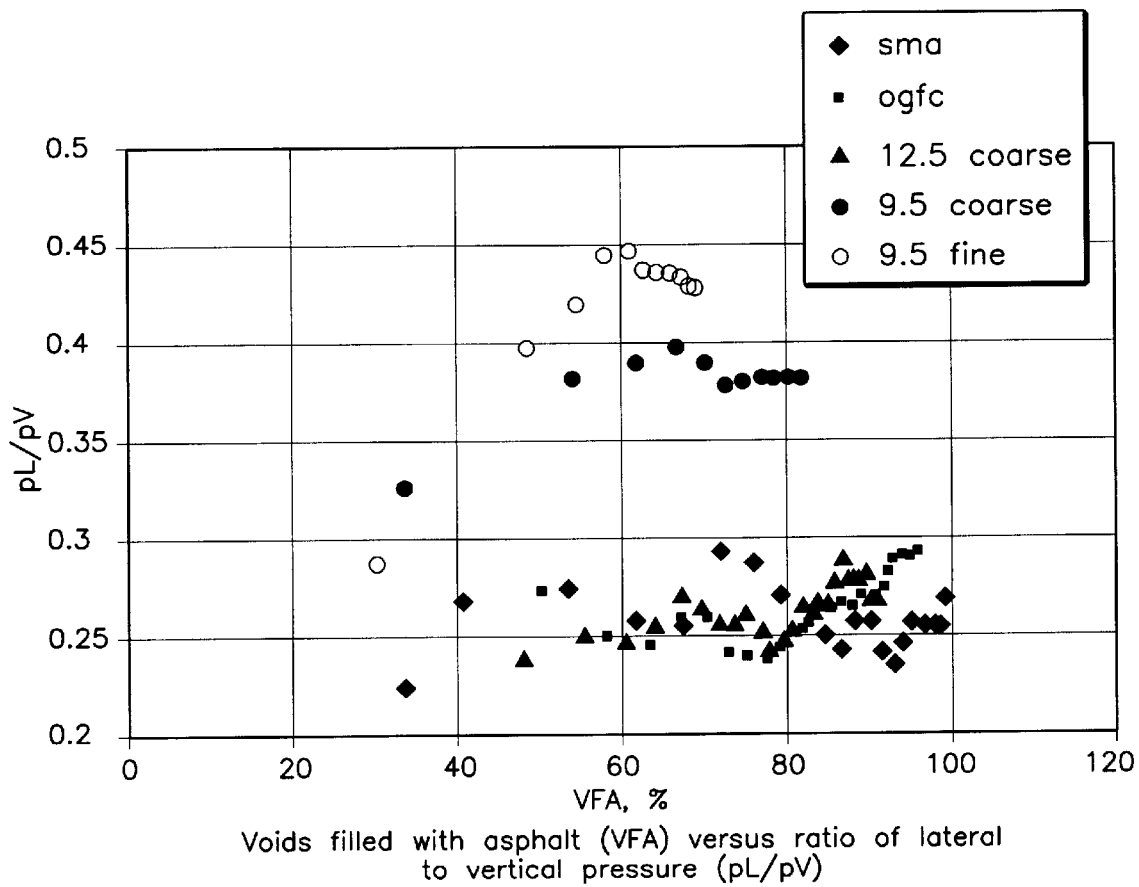
FIG. 18 is a plot of VFA versus pL/pV.

Finally, an open graded friction course (OGFC) mix with six percent asphalt content was compacted with the instrumented mold in the SGC. FIG. 18 shows the change in pL/pV with VFA, along with the same data for other mixes. It can been seen that coarser the mix, the less sensitive the pL/pV values are to a change in VFA—the fine mix with 9.5 mm nominal maximum aggregate shows the highest change and value of pL/pV at high VFA, whereas the SMA, which is the coarsest of all the mixes, show almost no effect of VFA and pL/pV values, in the range of VFA considered.

The results from the study carried out to evaluate the lateral pressure indicator (LPI) indicate that the LPI is sensitive to asphalt content, nominal maximum aggregate size, gradation and aggregate particle shape. It shows that there is an increase in lateral pressure, and hence reduction in shear strength with increase in asphalt content, use of rounded aggregates, and at air voids lower than 2 percent.

Although the foregoing description is made with specific reference to the testing of asphalt mixes, it is understood that the invention and application of the principles of the invention is not limited to this particular material or type of material.

What is claimed is:

1. A device for measuring reactive forces of a material subjected to a testing force, comprising:
    (a) a mold capable of housing material to be tested adapted for use with material testing equipment, the mold having a mold wall, a portion of the mold wall having an aperture defined by a perimeter within the mold wall area;
    (b) a movable insert piece capable of movement relative to the mold wall, wherein the movable insert piece is placed within the aperture; and
    (c) a sensor operative to measure force exerted on the insert piece by material in the mold.

2. The device of claim 1 wherein the mold is generally cylindrical having a cylindrical wall which forms a mold cavity.

3. The device of claim 1 wherein the insert piece is generally rectangular.

4. The device of claim 1 wherein the insert piece is generally circular.

5. The device of claim 1 wherein the insert piece is initially contiguous with an interior surface of the mold.

6. The device of claim 1 wherein the insert piece has an interior surface curved to match the contours of an interior surface of the mold.

7. The device of claim 1 wherein the insert piece is configured to interact with a sensor.

8. The device of claim 1 wherein the sensor is a load cell.

9. The device of claim 1 wherein the sensor is a strain gauge.

10. The device of claim 1 wherein the insert piece is held in position by bracketry.

11. The device of claim 9 further comprising a bracket attached to the mold proximate to the insert piece whereby the insert piece is retained within the surrounding wall of the mold.

12. A device for measuring reactive forces of a material subjected to a testing force, comprising:
    (a) a mold capable of housing material to be tested adapted for use with material testing equipment, the mold having a mold wall, the mold wall having a plurality of apertures, each aperture defined by a perimeter within the mold wall area;
    (b) a plurality of movable insert pieces capable of movement relative to the mold wall, wherein one of the movable insert pieces is placed within each aperture; and
    (c) a plurality of sensors operative to measure force exerted on the insert pieces by material in the mold.

13. The device of claim 12 wherein the mold is generally cylindrical having a flat bottom and a cylindrical wall which forms a mold cavity.

14. The device of claim 12 wherein the mold wall has two apertures.

15. The device of claim 12 wherein the apertures are spaced apart from each other radially along the mold wall.

16. The device of claim 15 wherein the apertures are spaced apart by approximately 90 degrees.

17. The device of claim 12 wherein the insert pieces are generally rectangular.

18. The device of claim 12 wherein the insert pieces are generally circular.

19. The device of claim 12 wherein the insert pieces are initially contiguous with an interior surface of the mold.

20. The device of claim 12 wherein the insert pieces have interior surfaces curved to match the contours of an interior surface of the mold.

21. The device of claim 12 wherein the insert pieces are configured to interact with sensors.

22. The device of claim 12 wherein the sensors are load cells.

23. The device of claim 12 wherein the sensors are strain gauges.

24. The device of claim 12 wherein the insert pieces are held in position by bracketry.

25. The device of claim 24 further comprising brackets attached to the mold proximate to the insert pieces whereby the insert pieces are retained within the surrounding wall of the mold.

26. A device for measuring reactive forces of a material subjected to a testing force, comprising:
    a) a mold capable of housing material to be tested adapted for use with material testing equipment, the mold having a mold wall, the mold wall having a more pressure-sensitive section and a less pressure-sensitive section, the more pressure-sensitive section being thinner than the less pressure-sensitive section;

b) a sensor operative to measure force exerted on the more pressure-sensitive section of the mold wall.

27. The device of claim 26 wherein the sensors are strain gauges.

28. A method of determining flow and load bearing characteristics of a material comprising the steps of:

a) placing a specimen of a material to be tested into a mold adapted for use with material testing equipment;

b) applying a force to the material in the mold;

c) attaching a sensor to a point on the mold not generally aligned with the direction of the applied force, to sense a pressure exerted by the material on the mold proximate to the point of attachment of the sensor; and d) determining a ratio between the applied force and the pressure exerted by the material on the mold.

29. The method of claim 28 wherein the mold is gyrated while applying a force to the material.

30. The method of claim 29 wherein the ratio is determined at gyration intervals.

31. The method of claim 28 further comprising using the ratio to determine rutting potential of the specimen.

32. The method of claim 28 further comprising using the ratio to predict performance of the specimen.

33. The method of claim 28, further comprising using the ratio to evaluate material properties of the specimen.

34. The method of claim 33, wherein material properties comprise aggregate size and shape.

* * * * *